United States Patent
Fuhr et al.

(10) Patent No.: US 8,304,228 B2
(45) Date of Patent: Nov. 6, 2012

(54) METHOD AND DEVICE FOR THE FORMATION OF BIOLOGICAL CELL MATERIAL

(75) Inventors: Günter R. Fuhr, Berlin (DE); Heiko Zimmermann, St. Ingbert (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 291 days.

(21) Appl. No.: 12/719,338

(22) Filed: Mar. 8, 2010

(65) Prior Publication Data

US 2010/0167382 A1 Jul. 1, 2010

Related U.S. Application Data

(62) Division of application No. 10/545,973, filed as application No. PCT/EP03/13580 on Dec. 2, 2003, now Pat. No. 7,704,741.

(30) Foreign Application Priority Data

Feb. 21, 2003 (DE) .................................. 103 07 487

(51) Int. Cl.
C12M 1/36 (2006.01)
C12M 1/38 (2006.01)
A61F 13/00 (2006.01)

(52) U.S. Cl. ............... 435/286.1; 435/289.1; 435/305.1; 435/395; 435/399; 435/400; 435/401; 604/305; 604/304; 623/1.12; 623/1.22

(58) Field of Classification Search ............... 435/289.1, 435/286.1, 305.1, 395, 399, 400, 401; 604/304, 604/305; 623/1.12, 1.22
See application file for complete search history.

(56) References Cited

U.S. PATENT DOCUMENTS

| | | | |
|---|---|---|---|
| 5,108,926 | A | 4/1992 | Klebe |
| 5,153,136 | A | 10/1992 | Vandenburgh |
| 5,641,644 | A | 6/1997 | Klebe |
| 5,792,603 | A | 8/1998 | Dunkelman et al. |
| 5,866,417 | A | 2/1999 | Matyas et al. |
| 5,900,361 | A | 5/1999 | Klebe |
| 6,576,458 | B1 | 6/2003 | Sarem et al. |
| 6,599,274 | B1 | 7/2003 | Kucharczyk et al. |
| 6,653,124 | B1 | 11/2003 | Freeman |
| 6,753,171 | B2 | 6/2004 | Karube et al. |
| 7,179,287 | B2 | 2/2007 | Wolfinbarger, Jr. |

(Continued)

FOREIGN PATENT DOCUMENTS

EP 0307085 A1 3/1989

OTHER PUBLICATIONS

Abercrombie et al., "The Locomotion of Fibroblasts in Culture", Experimental Cell Research, vol. 67 (1971), pp. 359-367.

(Continued)

*Primary Examiner* — Nathan Bowers
(74) *Attorney, Agent, or Firm* — Caesar, Rivise, Bernstein, Cohen & Pokotilow, Ltd.

(57) ABSTRACT

A manipulation tool is disclosed for producing cell material having multiple biological cells, which have a predefined geometrical arrangement. The tool includes a tool body, whose surface at least partially contacts the cell material, and a setting device for adjusting the tool body by a continuous expansion, so that geometrical properties of the surface change and an interior of the tool body is enlarged. The setting device is adapted to expand the tool body at an advance velocity in a range from 0.1 μm/h to 1 mm/h.

5 Claims, 3 Drawing Sheets

U.S. PATENT DOCUMENTS

| | | |
|---|---|---|
| 7,494,482 B2 | 2/2009 | Orgill et al. |
| 2005/0158845 A1 | 7/2005 | Wikswo et al. |
| 2006/0051735 A1 | 3/2006 | Fuhr et al. |
| 2006/0134600 A1 | 6/2006 | Fuhr et al. |
| 2008/0300571 A1 | 12/2008 | LePivert |
| 2009/0192454 A1 | 7/2009 | Boland et al. |

OTHER PUBLICATIONS

Cramer, "Organization and polarity of actin filament networks in cells: implications for the mechansim of myosin-based cell motility", Biochem. Soc. Symp., vol. 65 (1999), pp. 173-205.

Fuhr et al., "Cell Traces—Footprints of Individual Cells during Locomotion and Adhesion", Biol. Chem., vol. 379 (1998), pp. 1161-1173.

International Search Report for PCT/EP03/13580.

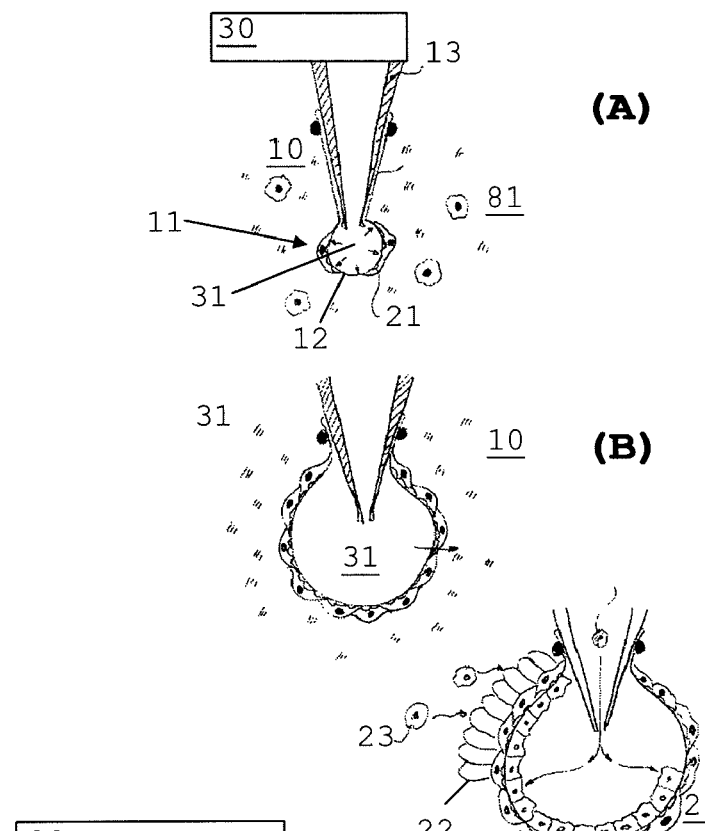
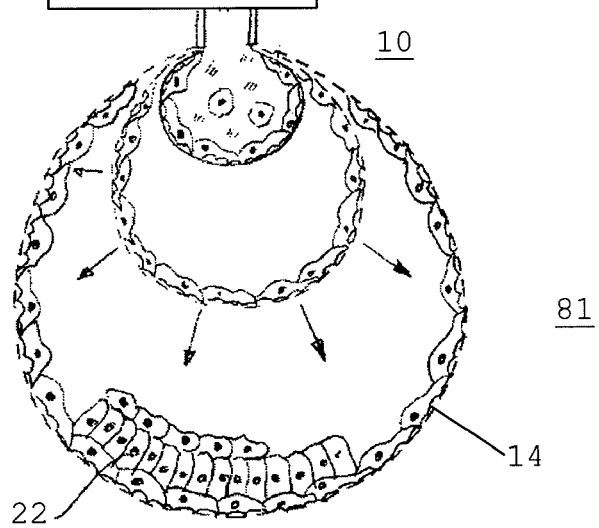
Fig. 1
Fig. 2
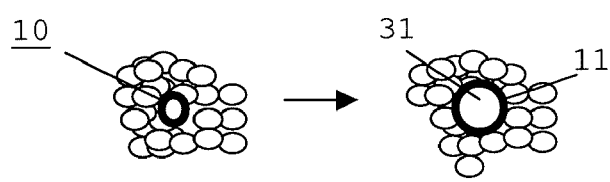
Fig. 3

METHOD AND DEVICE FOR THE FORMATION OF BIOLOGICAL CELL MATERIAL

BACKGROUND OF THE INVENTION

The present invention relates to methods for forming, particularly for shaping and/or depositing, cell material having multiple biological cells, particularly methods for setting or changing a surface topography of a cell material and methods for geometrical structuring of cell material, such as methods for tissue engineering. The present invention also relates to manipulation tools for performing these methods, particularly substrates for cell material, such as cell cultures or tissue, and shaping tools, using which the geometrical shape and/or dimensions of the cell material are changeable. The present invention also relates to novel applications of the cited methods and manipulation tools.

In medicine, biotechnology, and biochemistry, essential objects exist in the examination or manipulation of biological cells, particularly in connection with medicinal cell therapy and tissue engineering, in that cell formations or cell groups are provided having a predefined geometrical arrangement of the individual cells. For example, the shape of a cell material which is implanted into an organism is to be tailored as well as possible to the geometrical conditions at the implantation location. Adapting the shape of the implant material by suitable mechanical trimming (cutting) from a cell culture is known from practice. However, this is disadvantageous since damage to the cells or the cell material may have undesired effects during the tissue regeneration after the implantation. In numerous experiments known from practice, the desired regeneration or new growth of a cell or tissue type did not occur, but rather, for example, an induction of tumors. It is assumed that induction of tumors as uncontrolled cell reproduction of cells, is encouraged by physical, chemical, or mechanical external influences at the implant location. These influences may not be implemented reproducibly or at least detected using the current technologies.

A further example of the shaping of cell material is the examination of active ingredients (testing of pharmacological active ingredients) on tissue models. Preferably, spheroids are used as tissue models, which may be produced as spherical formations through layered growth of cell material on an inner core made of cells. A disadvantage of conventional tissue models is their restricted size. For example, until now only spheroids up to a diameter of approximately 150 µm have been able to be used. At larger diameters, problems arise in the nutrient supply of the inner cells. The vitality of the inner cells is restricted and dying of the cells from the inside to the outside may occur.

A further object in tissue engineering which has not been achieved up to this point is the production of structured composite material from cell materials of different types of cells or from biological cells and synthetic materials. A disadvantage is that up to now composite formations have been associated with mechanical injuries of cells or cell material.

The objects cited in cell therapy and the results in tissue engineering, which have been partially unsatisfactory up to this point, currently represent the most important restrictions and delays of a broad application of these methods in biotechnology and medicine.

The object of the present invention is to provide improved methods for forming cell material having a predefined geometrical arrangement of the individual cells, using which the disadvantages of conventional methods are overcome and which are particularly capable of shaping and/or generating cell material without injuring individual cells. It is also the object of the present invention to provide improved manipulation tools for performing methods of this type, using which the disadvantages of conventional cell or tissue technologies are overcome. It is a further object of the present invention to specify novel applications of the shaping, cultivation, or generation of cell material.

These objects are achieved by methods and manipulation tools having the features of the present invention.

SUMMARY OF THE INVENTION

In regard to the method, the present invention is based on the general technical teaching of setting the geometric arrangement of cells in the cell material using a manipulation tool, which at least partially contacts a cell material to be manipulated, by changing the surface geometry of the manipulation tool in a predefined way. The surface geometry may be changed according to the present invention in regard to at least one of the features of area, orientation in relation to a fixed reference system, surface shape, and surface structure. The cells of the cell material which contact the tool surface advantageously follow the surface movement, wherein the cells remain unchanged in their physical and chemical state during the surface movement. The geometrical change of the tool surface exclusively causes a rearrangement of the cells, particularly an injury-free displacement or shifting of cells, in which cells in contact with the tool body or cells lying deeper in the cell material are deformed or changed in their spatial position, but do not release any chemical signals in the form of messenger substances or substance secretions.

Cell material is generally understood here as an accumulation of cells which are connected to their environment via adhesion contacts (macromolecular chemical bonds, no van der Waals bonds). The cell material is, for example, a composite or aggregation of individual cells, a tissue (combination of identical differentiated cells), or an organ. The non-liquid composite of individual cells may additionally contain synthetic components, such as a synthetic matrix material. The formation of cell material is generally understood here as a change of the shape, density, size, and/or structure of cell material.

The manipulation tool is generally a foreign body or object made of a material which may be delimited in relation to the cell material having a fixed surface, whose geometrical properties are changeable at least in partial regions. The manipulation tool may, for example, have a substrate for cell culture, a probe in the cell material, or a stamp for shaping. The manipulation tool is adjustable in such a way that geometrical properties of its surface change in regard to at least one of the above-mentioned features. The velocity of the adjustment is referred to as the advance velocity.

The present invention is particularly based on the following considerations of the inventors. It was first recognized that the reactions of cells in a tissue or a cell composite, for example, which have had different results up to now, are caused as cells in the existing cell material are injured or destroyed by introducing a tool and wound effects are thus induced. In the event of a cell or tissue injury, chemical signals (emission of molecular messenger substances) or cellularly supported processes, such as a fibroplast immigration, a fibronectin excretion, or the like are generated. The reaction of injured cells influences the effect of the cells or additives. For example, stem cells behave differently in the environment of a cell injury than stem cells in intact cell material. Secondly, the inventors have found that, contrary to current expectations, even adhesively bonded cells may be spatially displaced without injury. This allows the mechanical insertion of tools into cell material. The cells remain uninjured during the movement of the tool surface in and/or through the cell material if the advance velocity is sufficiently low that adhesion contacts between the cells detach in natural ways, i.e., ways which do not influence or destroy the cells, and may be reformed in the changing environment.

The above-mentioned requirements may be completely fulfilled by the geometrical adjustment of the tool surface and the injury-free displacement or shifting of cells associated therewith. Damage or impairment of the cell material is excluded. The physical, chemical, and mechanical state of the cells may be completely characterized and maintained. Damaging contacts between cells and surfaces of foreign bodies are avoided, cellular signals due to undesired surface contacts are suppressed. The cell manipulation is performed extremely carefully by the injury-free movement. The manipulation tool may be guided accurately into a specific configuration in the cell material.

According to a preferred embodiment of the present invention, the manipulation tool is adjusted at a advance velocity which is less than or equal to a reference velocity determined by the physiological bonding rate of biological cells (bonding velocity of the cells during their natural cell movement). The natural cell movement (cell locomotion) includes the change in location of a complete cell on a fixed surface or in cell material by a rearrangement of adhesion contacts of cell organs (membrane organs, such as membrane protuberances), as are described, for example, by M. Abercrombie et al. in the publication "The Locomotion Of Fibroblasts In Culture" ("Experimental Cell Research", Vol. 67, 1971, pages 359-367) and by L. P. Cramer in the publication "Organization and polarity of actin filament networks in cells: implications for the mechanism of myosin-based cell motility" ("Biochem. Soc. Symp." Vol. 65, 1999, pages 173-205).

The physiological reference velocity is known per se (see, for example, G. Fuhr et al. in "Biol. Chem.", 1998, Vol. 379, pages 1161-1173) or measurable on animal or human cells. The bonding rate of interest may be derived by measuring the dynamics of adhesion patterns of individual cells on artificial surfaces, for example.

The advance velocity generally refers here to the velocity at which the surface of the manipulation tool moves in relation to the cell material. This velocity may relate to the entire surface per se, specific shaping elements, which represent parts of the surface, or a surface enlargement. In the event of a surface expansion, the advance velocity refers, for example, to the relative velocity of reference points during an enlargement of the surface. Upon adjustment of the advance velocity, the manipulation tool may advantageously move or rearrange cells in a naturally occurring composite without injury. The advance velocity is adapted to the cell movement occurring permanently in the tissue. For example, it is known that specific types of immune cells (e.g., macrophages), may move even through dense tissue by displacing existing cells. The inventors have found that surprisingly this displacement movement may also be implemented using probes which are significantly larger than immune cells and have macroscopic dimensions in the submillimeter to centimeter range, if the cited advance velocity is set. During the movement or production of the tool surface, macromolecular bonds running between the cells (for example, membrane-related macromolecules of the integrin and cadherin families) are separated and relinked to the probe surface, for example.

Special advantages of the present invention result if the advance velocity of the manipulation tool is selected in a velocity range from 0.1 μm/h to 1 mm/h, preferably in the range from 1 μm/h up to 500 μm/h. The bonding rates of the formation and breakdown of macromolecular bonds, which are typically mediated by membrane-related macromolecules of the integrin and cadherin families, lie in this velocity range. The preferred velocity ranges correspond to the velocities of the cell movement of fibroplasts, macrophages, lymphocytes, chondrocytes, or tumor cells in particular. Advantageously, if a advance velocity this low is set, the position and shape of the tool surface may be set at a high precision of approximately +/−1 μm or even less. The propulsion velocities in the cited ranges correspond to the active endogenic movement velocities of cells in and on tissue. The movement of the probe thus causes a permanent formation and restructuring of the cells in the direct environment of the probe surface, displacement of the cells being encouraged by the permanently acting advance force.

If the manipulation tool is subjected to a permanently acting advance force, its movement at the desired advance velocity may advantageously be performed even with the lowest application of force. This allows the use of drive devices having low power. If the advance force is formed by a mechanical pressure force, advantages for the transmission of the advance force to the probe may result. If the advance force is formed by forces in electrical or magnetic fields, advantages may result for the construction of an injection device, since the advance forces may be exerted via remote action.

Special advantages may result if the method according to the present invention is executed on cell material which is located outside an animal or human organism. The cell material may be positioned under suitable cultivation conditions on a fixed carrier, which applies the counterforce to the exertion of the advance force. The cell material and the probe may be positioned with higher precision.

Alternatively, the cell material may be located in the composite in a living organism. The manipulation tool may, for example, be inserted as an examination probe, biopsy tool, or injection tool into tissue. The insertion occurs, because of the low advance velocity, in a state in which the affected tissue is held fixed in one location on a carrier, e.g., with the surrounding part of the organism. The use of an anesthetic is preferred for the immobilization, but is not absolutely necessary in regard to the freedom of injury of the method, however.

According to a further preferred embodiment of the present invention, the adjustment of the manipulation tool may comprise an expansion of the tool surface. The cell material to be manipulated is positioned on the tool surface. The cell material forms a cell layer whose thickness is reduced by the expansion of the surface and/or in which gaps arise in which the tool surface is exposed. Advantageously, the production of an enlarging layer composite of the cell material is thus made possible through growth of cells from an adjoining cultivation medium. This embodiment of the present invention may therefore particularly have advantages for providing the above-mentioned tissue model for active ingredient testing.

According to a first variant, the manipulation tool is at least partially made of an elastic material which forms the tool surface which contacts the cells and which is stretched during the manufacture of the manipulation tool. The elastic material (e.g., plastic, rubber) advantageously forms a closed, continuous surface. Alternatively, according to a second variant, the adjustable surface may be made of a nonelastic material, such as lamellae made of metal or plastic which are displaceable into one another, advantages for the precision of the change of the geometric surface properties able to result.

If, according to a further modification of the present invention, the manipulation tool has a hollow body which has an inner cavity with an inner surface which is enlarged during the adjustment of the manipulation tool, advantages may result for providing spheroidal tissue models. According to different variants of the present invention, the cell material may be positioned externally on the hollow tool body, on the inner surface of the tool body, or on both inner and outer surfaces. These variations have advantages for providing layered tissue models made of different types of cells, which may grow from the outside or the inside on the tool surface, the substrate area available being continuously enlarged through the adjustment of the surface according to the present invention. An undesired high layer thickness, which may result in insufficient supply of lower lying cells, may advantageously be avoided, significantly larger spheroids than in typical tissue models simultaneously being able to be produced.

The hollow manipulation tool is preferably made spherical with a diameter in the range from 0.01 mm to 10 cm.

If, according to a further variation of the method according to the present invention, the formation of the cell material comprises the geometric rearrangement of the cells by adjusting the tool surface and simultaneous growth of cells from a surrounding medium, advantages for the generation of cell cultures having a predefinable maximum thickness may result. Accordingly, an independent object of the present invention is a cell cultivation method in which cells from a cultivation medium grow on an enlarging substrate surface. Special advantages may result for tissue engineering if the cell material is produced in layers on or in the hollow tool body from different types of cells.

The tool surface may be enlarged by exerting a hydrostatic pressure on the interior of the manipulation tool. For example, according to an advantageous variation of the present invention, the hollow tool made of an elastic material may be connected to a pressure line (such as a liquid line), through which a liquid or a gas may be introduced into the interior of the tool under pressure. The stretching of the tool surface is performed by supplying liquid or gas. The stretching using a liquid has the advantage that the supply liquid volume is directly associated with the enlargement of the surface. For the above-mentioned deposition of cell material on the interior of the hollow body, it may be advantageous if a cell suspension, which conveys the cells to be cultivated into the interior, is used as the liquid for stretching the tool surface.

For the application in tissue engineering, it may be advantageous if the surface of the tool body is made of a material which allows an electro-physiological contact, a substance transfer between the interior of the tool and its environment, and/or cell contacts between the interior and exterior.

According to a further, preferred embodiment of the present invention, the tool body contains at least one displaceable shaping element, the shaping element projecting out of the tool surface upon the adjustment of the tool body and thus changing the surface design. The at least one shaping element provides the tool body with the function of a plunger, whose plunger shape may be adapted variably to the particular requirements by the displaceability of the shaping element. If multiple shaping elements are provided, the variability in the design of the plunger surface is advantageously elevated.

According to a variant of the present invention, the tool having the at least one shaping element may be used as a cell culture carrier which determines the shape of the cell culture. Alternatively, the manipulation tool having the surface whose shape is determined by the position of the at least one shaping element may be pushed onto the cell material like a plunger.

An independent object of the present invention is a biological cell material or cell-carrier composite material produced using the method according to the present invention, such as a cell spheroid which is formed by a cell material on an expanded carrier surface.

In regard to the device, the above-mentioned object is achieved by providing a manipulation tool which comprises a tool body having at least one surface, whose shape and/or size is adjustable, and a setting device for adjusting the surface. Advantageously, upon contact with a cell material to be manipulated, this tool allows the cell material to be embossed with the surface design. If the setting device for changing the surface geometry is set up having a characteristic advance velocity corresponding to a physiological reference velocity of biological cells, the above-mentioned advantages result for injury-free rearrangement of the cells during the shaping.

According to an especially advantageous variant, the surface of the manipulation tool is provided with a structure or coating which encourages an adherent adhesion of biological cells. The bonding material forms the tool body, at least the front of the tool body, or a coating on at least on the front of the tool body. It is made of, for example, fibronectin or collagen. This embodiment of the present invention may have advantages in regard to elevation of the bonding speed during the displacing movement of the probe through the cell material. The bonding material may alternatively have characteristic structure sizes in the sub-μm range, due to roughening, so that the bonding of the cell material to the probe is encouraged.

The surface of the manipulation tool may additionally be equipped with a structure or coating which blocks an adherent adhesion of biological cells at least in partial regions of the surface. For example, chemical compounds known per se, such as hydrophobic silanes and hydrophilic polymers, are provided as the coating.

BRIEF DESCRIPTION OF SEVERAL VIEWS OF THE DRAWINGS

Further details and advantages of the present invention are described in the following with reference to the attached drawings.

FIGS. 1 and 2 show illustrations of the production and rearrangement of cell material according to a first embodiment of the present invention, FIG. 3 shows an illustration of a radial expansion movement of a manipulation tool according to the present invention.

DETAILED DESCRIPTION OF PREFERRED EMBODIMENTS

Figure 4:
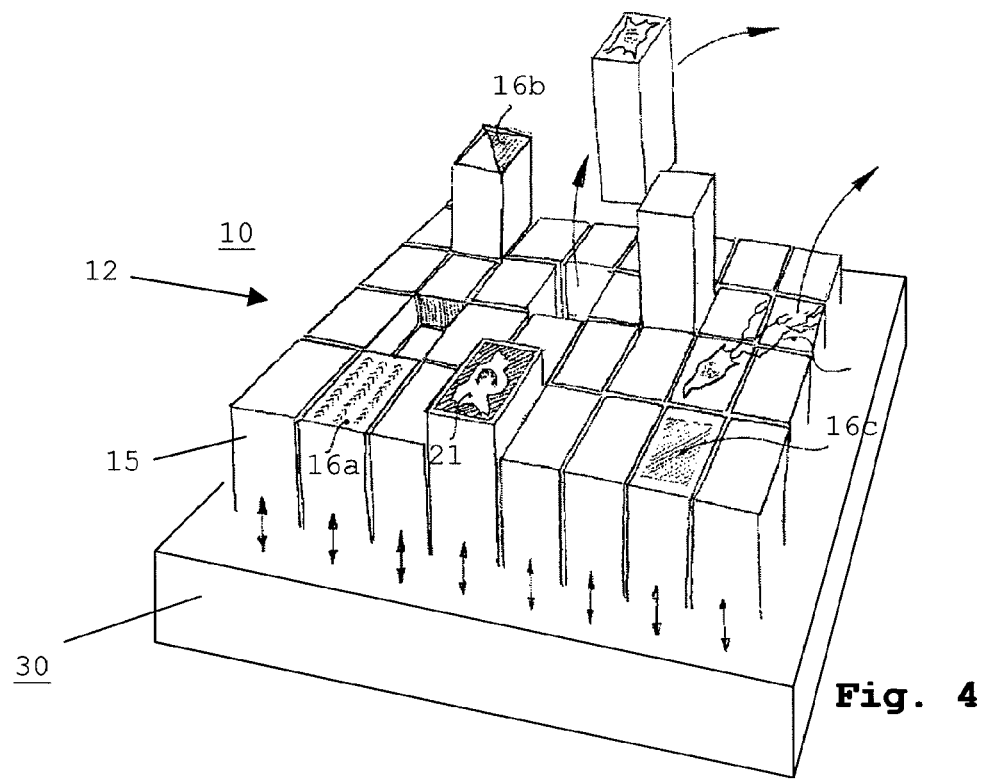
FIGS. 4 and 5 show an illustration of a tool surface having multiple displaceable shaping elements.

FIGS. 1 and 2 illustrate the principle according to the present invention of generating hollow spheres or other hollow geometries from cell material in a predefined way. For this purpose, a manipulation tool 10 is provided having an elastic, hollow tool body 11 and a pressure line 13, via which an external pressure source 30 (only shown in partial image A) is connected to the interior 31 of the tool body 11. The schematically shown pressure source 30 forms an setting device for adjusting the surface 12 of the tool body 11. It comprises a liquid reservoir and a pump, for example.

The tool body 11 forms a balloon made of rubber, for example, which has a diameter of 0.01 mm in the relaxed state, for example, and may have diameter of up to 100 mm in the stretched state, for example. A capillary made of steel or glass, for example, is used as the pressure line 13. If the material of the tool 10 comprises partially-permeable, elastic plastic material (e.g., silicone membrane), the generation of material gradients in the cell tissue is advantageously made possible.

By injecting air or a liquid into the interior 31, the surface 12 of the tool body 11 may be enlarged, the shape being essentially maintained. The enlargement occurs in such a way that neighboring reference points on the surface 12 move apart from one another at a velocity corresponding to the above-mentioned physiological reference velocity. Correspondingly, cells on the surface 12 may follow the stretching movement without being subjected to undesired mechanical destruction. Partial images A and B of FIG. 1 show how a monolayer of cells 21 from a surrounding cell suspension 81 initially grows on the surface 12 of the relaxed tool body. By enlarging the surface 12, the space for enlarging the cell monolayer 20 is continuous enlarged.

By adding further cell types 22, 23 to the external medium and/or the internal medium, flexible tissue-type cell layers may be generated, as a schematically illustrated in partial image C.

FIG. 2 shows the cultivation of cell material 20 on the inner surface 14 of the hollow body 11 in three different expansion states. The cavity 31 is filled with a cell suspension from the liquid reservoir of the pressure source 30 via the pressure line 13. Adherent growing cells (e.g., fibroblasts, macrophages, or tumor cells) actively colonize the inner surface 14. For many types of cells, a contact inhibition occurs when the substrate surface is completely covered. This means that further reproduction is ended as soon as a monolayer has been formed. Through the stretching of the tool surface according to the present invention, this process may be controlled in a targeted way.

The interior 31 may be charged with different types of cells sequentially or simultaneously, as is shown in the largest stretching variation in FIG. 2, so that a cell material similar to tissue, having a function corresponding to the types of cells participating in the formation of the cell material is generated. In this variation as well, the interior 31 may be in electrophysiological contact with the external medium 81.

FIG. 3 shows an example of a radial expansion movement of a capillary-shaped tool 10, whose body 11 is made of an elastic material (such as plastic, rubber) or a non-elastic expandable material (such as lamellae made of steel or plastic or the like which are displaceable in relation to one another). By a pressure elevation in the hollow channel 31 of the tool 10, its diameter may be expanded, injury-free displacement of the cells occurring. The diameter of the tool body 11 enlarges at the advance velocity described above.

Figure 5:
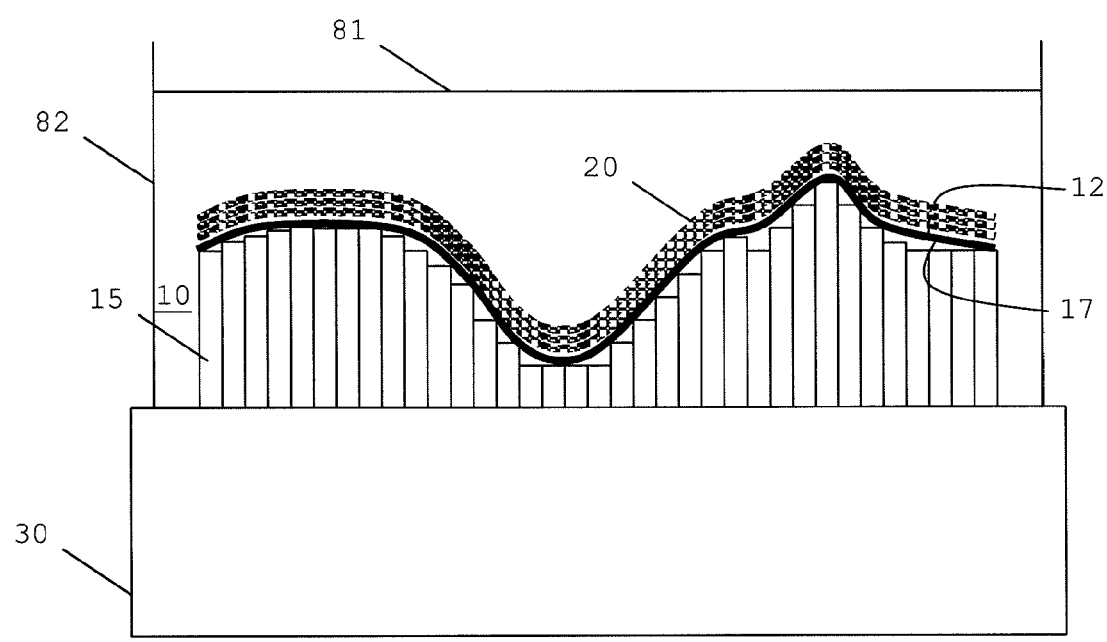

FIGS. 4 and 5 illustrate a manipulation tool 10 which has multiple shaping elements 15, each of which is individually displaceable using an setting device 30, which is attached to a base part (not shown). Each shaping element 15 has a cuboid shape having a top 16. The total number of the tops 16 or at least a yielding, layered cover element 17 positioned thereon (see FIG. 5) form the surface 12 of the manipulation tool 10, which is used for shaping cell material 20. The shaping elements 15 form the tool body. The tops 16 have typical dimensions in the range from 0.01 mm to 5 mm. The shaping elements 15 are oriented so that the tops 16 form a matrix arrangement made of linear rows and columns. The displacement of the shaping elements 15 in relation to the base part is performed using positioning motors or piezoelectric drives, for example. The tool surface is structured depending on the selected propulsion of a shaping element 15. Individual shaping elements 15 may be separable from the setting device 30 in order to form holes in the cell material, for example.

The cover element 17 has the advantages that the tool surface is smoothed locally and the removal of the cell material from the tool is made easier. The cover element 17 comprises a film (such as polyurethane) or a membrane, for example, which extends over all shaping elements 15 and on which the cells are positioned. Alternatively, one or more cover elements 17 may be provided, which only extend over one or more partial groups of shaping elements 15. Removable adhesion of the cover element 17 to some or all tops 16 of the shaping elements 15 may be provided.

The cover element 17 may be made of a synthetic polymer material and/or of a material occurring naturally in biological organisms, such as chitin or bone matrix material, in one or more layers. The cover element 17 may also carry a structured coating which encourages adherent adhesion of biological cells in partial regions and blocks it in other regions.

For the production according to the present invention of cell material, the cell material is first positioned on the tool surface 12, i.e., on the entirety of the tops 16 or the joint cover element 17. For this purpose, for example, growth from a cultivation medium 81 in a culture vessel 82 (see FIG. 5) is provided. For reasons of clarity, only individual cells 21 are shown in FIG. 4. The surface of the manipulation tool 10 is subsequently adjusted by advancing the shaping elements 15 into the particular desired positions. This advance occurs at the above-mentioned physiological reference velocity, so that during the deformation of the cell material, injury-free displacement and rearrangement of the cells occurs. Subsequently, the cell material may be detached from the manipulation tool 10.

FIG. 4 also illustrates that the individual tops 16 of the shaping elements 15 may be formed differently in order to additionally modify the cell material at the particular positions. For example, microstructures (see at 16a) may be provided for improving the adhesion capability of the tops 16 or additional structure elements, such as the pyramid shape 16b, may be provided to make a structure in the cell material. Furthermore, individual or all shaping elements 15 may carry an adhesion-promoting coating 16c.

Figure 6:
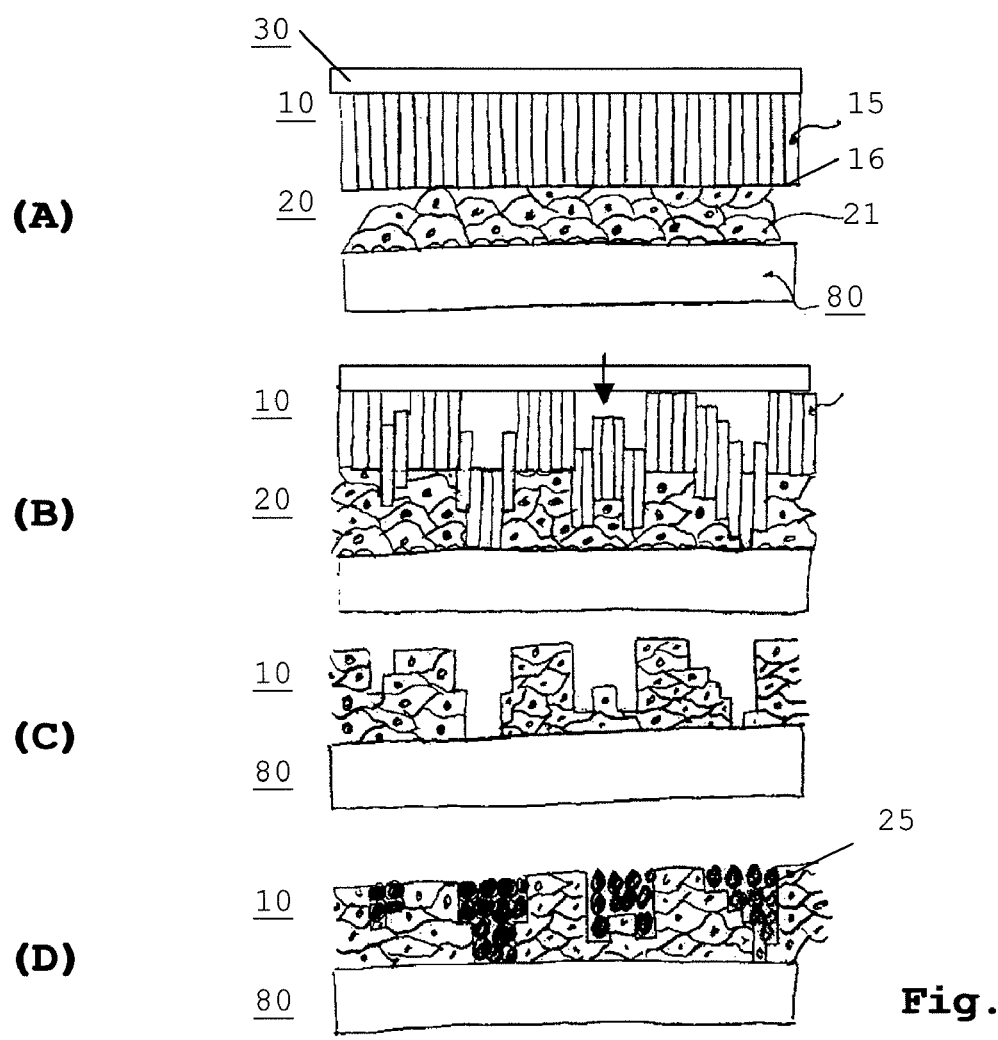
FIG. 6 shows a shape embossing of cell material according to the present invention using a manipulation tool.

A manipulation tool as shown in FIG. 4 may alternatively be used as an imprinting tool, as is illustrated in the image sequence shown in FIG. 6. In a starting situation as shown in partial image A, a cell material 20 is located on a carrier 80, which is to be deformed in accordance with the method according to the present invention. The manipulation tool 10 having multiple displaceable shaping elements 15 is positioned over the initially free surface of the cell material 20. The manipulation tool 10 is moved toward the cell material 20 until the tops 16, which point downward in this case, contact the cell material 20. Subsequently, as shown in partial image B, the surface 11 of the manipulation tool 10 is adjusted through the targeted propulsion of individual shaping elements 15. The advance movement is performed at the above-mentioned physiological reference velocity of biological cells. The individual shaping elements 15 displace the cells in the cell material without injury.

Subsequently, as shown in partial image C, the manipulation tool 10 is removed. The surface shape of the tool remains in existence as a complementary structure in the cell material 10. To make it easier to separate the manipulation tool 10 from the cell material 20, the tops 16 of the shaping elements 15 may be provided with a coating on which adhesion of cells is suppressed. The coating is performed, for example, using the polymer Polyhema. Finally, the gaps introduced into the cell material may be filled with other cells or a synthetic matrix material 25 as shown in partial image D.

The shape and cells or additives 20 possibly supplied in the cell material are selected depending on the concrete task in the scope of the tissue engineering. For example, using the sequence shown in FIG. 6, epithelial cells having a predefined structure may be connected to tissue cells.

The features of the present invention disclosed in the above description, the claims, and the drawing may be significant both individually or in combination for implementing the present invention in its various embodiments.

What is claimed is:

1. A manipulation tool for producing a hollow cell material comprising multiple biological cells having a predefined geometrical arrangement, said manipulation tool comprising:
    a hollow tool body having a form of a hollow balloon and having at least one surface, said surface being arranged for accommodating at least one cell layer of adherently growing cells; and
    a setting device arranged for an adjustment of the tool body by a continuous expansion, so that geometrical properties of the at least one surface change, and an interior of the tool body is enlarged,
    wherein the setting device is adapted to continuously expand the tool body at an advance velocity in a range from 0.1 μm/h to 1 mm/h.

2. The manipulation tool according to claim 1, wherein the advance velocity is less than or equal to a physiological reference velocity of the cells.

3. The manipulation tool according to claim 1, wherein the tool body comprises an elastic material.

4. The manipulation tool according to claim 1, wherein the tool body comprises a non-elastic, expandable material.

5. The manipulation tool according to claim 1, wherein the tool body is connected to a pressure source via a pressure line.

* * * * *